(12) United States Patent
Wunderlich et al.

(10) Patent No.: US 10,260,915 B2
(45) Date of Patent: Apr. 16, 2019

(54) CONTAINER WITH SENSOR ARRANGEMENT

(71) Applicant: Endress+Hauser Conducta GmbH+Co. KG, Gerlingen (DE)

(72) Inventors: Ingrid Wunderlich, Radebeul (DE); Christian Fanselow, Geringswalde (DE)

(73) Assignee: Endress+Hauser Conducta GmbH+Co. KG, Gerlingen (DE)

( * ) Notice: Subject to any disclaimer, the term of this patent is extended or adjusted under 35 U.S.C. 154(b) by 71 days.

(21) Appl. No.: 15/278,621

(22) Filed: Sep. 28, 2016

(65) Prior Publication Data

US 2017/0089740 A1    Mar. 30, 2017

(30) Foreign Application Priority Data

Sep. 28, 2015 (DE) .................. 10 2015 116 355

(51) Int. Cl.
*G01D 11/24* (2006.01)
*B65D 25/02* (2006.01)
*G01N 27/416* (2006.01)

(52) U.S. Cl.
CPC ........... *G01D 11/245* (2013.01); *B65D 25/02* (2013.01); *G01N 27/4167* (2013.01)

(58) Field of Classification Search
CPC ............ G01N 33/0006; G01N 33/007; G01N 27/4163; G01N 24/4165; G01N 27/4167; G01D 11/245; B65D 25/02
USPC ...................... 73/431, 1.02, 1.03, 1.06, 1.07, 73/864.53–864.59, 866; 374/139, 140, 374/208, 209; 324/437, 438, 601, 130
See application file for complete search history.

(56) References Cited

U.S. PATENT DOCUMENTS

| 4,442,706 A | * | 4/1984 | Kawate | .................... C21B 7/06 266/99 |
| 5,188,803 A | * | 2/1993 | Hochberg | .......... A61B 5/14542 422/501 |
| 2004/0211251 A1 | * | 10/2004 | Lee | .................. G01N 33/54373 73/146.3 |
| 2006/0131765 A1 | | 6/2006 | Terentiev et al. | |

(Continued)

FOREIGN PATENT DOCUMENTS

| CN | 102971622 A | | 3/2013 |
| DE | 3023427 | * | 1/1981 |

(Continued)

OTHER PUBLICATIONS

Search Report for German Patent Application No. 10 2015 116 355.1, German Patent Office, dated Aug. 3, 2016, 7 pp.

*Primary Examiner* — Robert R Raevis
(74) *Attorney, Agent, or Firm* — Kelly J. Smith; PatServe

(57) ABSTRACT

A container for use as a single-use component in a processing system for performing a biological, biochemical, or biotechnological process includes a wall surrounding a container interior space with a sensor arrangement integrated into the wall, where the sensor arrangement includes at least one sensor and one housing, and where the housing includes a housing wall, which surrounds a housing interior space containing the sensor and separates the housing interior space from the container interior space, characterized in that the housing wall comprises a wall region, which is designed as a predetermined breaking point.

12 Claims, 2 Drawing Sheets

(56) References Cited

U.S. PATENT DOCUMENTS

| | | |
|---|---|---|
| 2007/0126794 A1 | 6/2007 | Schick et al. |
| 2011/0124035 A1 | 5/2011 | Broadley et al. |
| 2011/0236962 A1 | 9/2011 | Loebbert et al. |
| 2016/0312170 A1* | 10/2016 | Adkins ................ G01N 27/283 |

FOREIGN PATENT DOCUMENTS

| | | | |
|---|---|---|---|
| DE | 199 09 242 A1 | | 8/2000 |
| DE | 10 2011 080 956 A1 | | 1/2013 |
| DE | 102016000997 | * | 2/2017 |
| EP | 939292 | * | 9/1999 |
| JP | 54-101553 | * | 8/1979 |
| WO | 2015/142805 A1 | | 9/2015 |

* cited by examiner

CONTAINER WITH SENSOR ARRANGEMENT

CROSS-REFERENCE TO RELATED APPLICATION

The present application claims priority to German Patent Application No. 10 2015 116 355.1, filed on Sep. 28, 2015, the entire content of which is incorporated herein by reference.

TECHNICAL FIELD

The present disclosure relates to process sensor arrangements, specifically process sensors and disposable process containers.

BACKGROUND

Pharmaceutical, biological, biochemical, or biotechnological processes are increasingly performed by means of so-called disposable process solutions—for example, in processing systems in single-use technology. Such processing systems comprise pipelines or reactors, which are designed as disposable containers, e.g., disposables or disposable bioreactors or single-use bioreactor or single-use component. Such disposable containers may, for example, be flexible containers, such as pouches, tubes, or fermenters. Bioreactors or fermenters frequently have supply and discharge lines, which are designed as tubes, for example. Stiff pipe sections may also be used in the supply and discharge lines. After a process is completed, the disposable containers may be disposed of. In this way, extensive cleaning and sterilization processes are avoided. The use of disposable containers in particular prevents the risk of cross-contaminations and thus increases the process reliability.

In order to monitor or control the processes, it may be necessary to measure physical or chemical measured variables of the media contained in the disposable process containers. To this end, optical as well as electrochemical—for example, potentiometric or amperometric—sensors or conductivity sensors are used. So-called multisensors have also proven to be advantageous, which are designed to measure several different measured variables. Such multisensors frequently comprise several sensing elements, wherein each sensing element is designed to detect measured values of one of the measured variables to be monitored.

The processes performed in the disposable containers take place in a closed system, i.e., without any connection to the surroundings outside the disposable container. Since sterile conditions are frequently required, the disposable containers must be sterilized prior to introducing the process media. For this purpose, gamma radiation is frequently used in biochemical, biological, biotechnological, and pharmaceutical applications. Even while the processes are taking place in a disposable fermenter or disposable reactor, the ingress of foreign substances—e.g., seed crystals—from the surroundings into the interior of the disposable container must be prevented, so that the process sequence is not impaired or adulterated. The same also applies to supply and discharge lines, which end in the disposable fermenter or disposable reactor or lead out of the disposable fermenter or disposable reactor.

One or more sensors integrated into the disposable container may be sterilized together with disposable container. As a result of the sterilization and/or in case the disposable containers and the integrated sensors are stored for a longer period of time after sterilization and before commissioning, the properties of the integrated sensors may change, which can result in a change in the respective sensor characteristic curves—for example, to a zero-point drift. Potentiometric and amperometric sensors frequently comprise diaphragms, which should ideally be stored under damp conditions in order to ensure that the sensor outputs reliable measured values immediately after commissioning.

Furthermore, the sterilization by means of gamma radiation required for many biochemical and biotechnological processes may result in the destruction of electronic components of the sensors. It has therefore been proposed, e.g., in DE 10 2011 080 956 A1, to design sensors integrated into the walls of disposable containers to be sterilized as disposable analog sensors and to removably connect them after the sterilization to an electronic unit that is arranged outside the disposable container, comprises non-sterilizable components, and is designed to further process the analog measured values provided by the sensor. After the process is completed, the electronic unit may be used further and may be connected to a new sterilized disposable sensor in a different processing system. Since the complete measuring section, which comprises the analog sensor and the electronic unit, does not exist until commissioning, an efficient calibration, verification, or even an adjustment of the sensors integrated into the disposable containers immediately prior to commissioning would also be desirable in such cases.

SUMMARY

The container according to the present disclosure comprises a wall surrounding a container interior space with a sensor arrangement integrated into the wall, wherein the sensor arrangement comprises at least one sensor and one housing, and wherein the housing comprises a housing wall, which surrounds a housing interior space containing the sensor and separates the housing interior space from the container interior space, characterized in that the housing wall comprises a wall region, which is designed as a predetermined breaking point.

The container may, for example, be a process container in single-use or disposable technology, as already described above. It may, in particular, be made of hygienically approved plastic and comprise a flexible or stiff wall. The container with the integrated sensor arrangement may be sterilized by means of gamma radiation of up to 50 kGy and commissioned immediately afterwards or stored prior to commissioning for a longer period of time. By arranging the sensor arrangement in a housing, the wall of which separates the sensor from the interior space of the container, the sensor is protected against environmental influences; in particular, a medium that counteracts an aging of or change in the sensor may be contained in the housing interior space, in which the sensor is arranged. For example, the housing interior space may contain a medium, e.g., an aqueous buffer solution, in which the sensor can be stored under damp conditions. This is, in particular, advantageous for amperometric and potentiometric sensors, which frequently comprise diaphragms. The storage under damp conditions allows for a quicker commissioning, since the sensors stored under damp conditions can immediately output reliable measured values with an acceptable response time. The medium contained in the housing interior space may also be used for a calibration, verification, or adjustment of the sensor, as described in more detail below.

During commissioning, the predetermined breaking point can be deliberately destroyed, and a connection can thus be established between the housing interior space and the container interior space. In this way, the sensor can be brought into contact with a measuring medium contained in the container interior space, in order to detect measured values. In the process, the medium contained in the housing interior space exits into the container interior space. It is therefore advantageous if the medium contained in the housing interior space is selected such that it does not impair the process performed in the container. For example, physiological buffer solutions are, as a rule, harmless to biotechnological processes, which are normally performed in disposable process containers, and may accordingly be used as media for the damp storage and/or calibration, verification, or adjustment of the sensor.

In one embodiment, the wall region designed as the predetermined breaking point is arranged in a section of the housing wall that protrudes into the container interior space.

The predetermined breaking point may, for example, be constituted by a notch in the housing wall. This notch may be arranged on the outside, i.e., the side facing the container interior, or on the inside, i.e., the side facing the housing interior space, or on both sides of the housing wall.

In an embodiment that is advantageous in combination with a multitude of sensor types, the housing is designed to be cylindrical, wherein the notch extends on the inside or outside of the housing circumferentially to the cylinder axis of the housing. In this embodiment, a portion of the housing wall constitutes a cylinder jacket of the cylindrical housing, on which the notch is arranged. Advantageously, the notch in this embodiment forms a closed line, such as a circle, through the center of which the cylinder axis of the housing extends, or an ellipse.

The predetermined breaking point may also be designed as a wall region with a wall thickness that is reduced compared to the rest of the housing wall, wherein the wall thickness is determined such that the wall region bursts if an over-pressure or under-pressure prevails inside the housing. An increase or reduction in pressure inside the housing may, for example, be produced by a movement—in particular, an axial movement—of the sensor in the housing interior space or by driving the sensor into the housing interior space, by means of which a medium contained in the housing interior space is compressed or expanded. Alternatively, an increase in pressure can be produced by adding medium to the housing interior space, or a decrease in pressure can be produced by removing medium from the housing interior space, until, where applicable, a vacuum develops in the housing interior space. The sensor arrangement may comprise means that are accessible from outside the container or operable from outside the container for increasing or decreasing the pressure inside the housing interior space.

In one embodiment, the housing of the sensor arrangement may be retained in an adapter, which is attached to the wall of the container and in which an accommodating channel is formed, which surrounds at least a section of the housing.

The housing may be guided in the accommodating channel so as to be able to move axially and/or be mounted rotatably about an axis of the accommodating channel or an axis of the housing. In one advantageous embodiment, the sensor arrangement and/or the adapter may be designed such that the predetermined breaking point breaks as a result of a movement of the housing relative to the accommodating channel and such that a connection is thereby established between the housing interior space and the container interior space, via which a process medium contained in the container interior space can reach the sensor.

The adapter may, for example, comprise an element that works together with the predetermined breaking point to open the housing toward the container interior space. This element may, for example, constitute a thrust bearing, which is designed such that it opposes a rotational movement or an axial movement of the housing by means of a mechanical resistance, which results in the breaking of the predetermined breaking point. The element may also be designed to cut open the housing wall in the vicinity of the predetermined breaking point, e.g., in a region in which the housing wall has a reduced wall thickness compared to the other regions of the housing wall, when the housing is moved axially and/or rotationally.

The section of the housing wall comprising the predetermined breaking point may be made of a plastic—for example, PE, PP, a fluorine-containing plastic, PVDF, or PFA.

The sensor may be designed to detect values of at least one measured variable of a measuring medium, wherein the housing interior space is filled with a medium—for example, a liquid—so that the sensor is at least partially wetted by the liquid. As already explained above, this allows for an advantageous damp storage of the sensor. This embodiment is, in particular, advantageous if the sensor comprises a diaphragm that must be protected against drying out, for example, for a multitude of potentiometric, amperometric, as well as optical sensor types.

In an advantageous embodiment, the medium may exhibit a predetermined value of the at least one measured variable that is to be monitored by means of the sensor. This allows for a calibration, verification, or adjustment of the sensor immediately prior to commissioning of the container with the integrated sensor arrangement.

The sensor may also be designed as a multisensor for detecting values of several—in particular, different from one another—measured variables, wherein the medium exhibits a respective predetermined value of the several mutually different measured variables. In this case, it may be advantageous if the medium contained in the housing exhibits a defined value for several or all of these measured variables, in order to calibrate, verify, or adjust the multisensor immediately prior to commissioning.

The housing comprises a supply line that ends in the housing interior space and that is accessible from outside the container. Via this supply line, the medium can be filled into the housing, e.g., for the purposes of the already mentioned pressure increase or for the case where the sensor is to be stored under dry conditions, but shortly before commissioning, a calibration, verification, or adjustment is to be performed by means of a medium to be introduced into the housing interior space. Alternatively, the supply line may also be used to extract the medium contained in the housing interior space for the damp storage of the sensor from the housing interior space, before a connection between the housing interior space and the container interior space is established by breaking the predetermined breaking point. In particular, a vacuum can be generated inside the housing via the supply line in order to break the housing at the predetermined breaking point. This embodiment prevents a medium contained in the housing interior space for the storage of the sensor from reaching a process performed in the container.

In one advantageous embodiment, the supply line may be closed off at the end that is accessible from outside the container by a sterile connector or by a sterile filter.

The sensor may comprise a potentiometric or an amperometric sensing element. Such sensing elements frequently comprise a measuring diaphragm, which ideally is to be stored under damp conditions, so that the container according to the present disclosure with the sensor arrangement is particularly suitable for the integration of sensors with such sensing elements.

The sensor may comprise several sensing elements of the same type—for example, several potentiometric sensing elements with different sensor zero-points.

In one embodiment, the sensor may be a potentiometric sensor, which comprises at least two pH-measuring half-cells and at least one reference half-cell, wherein the potential difference detectable between the reference half-cell and a first of the two pH-measuring half-cells as a function of the pH value of a measuring medium in contact with the sensor comprises a first sensor zero-point, and wherein the potential difference detectable between the reference half-cell and the second of the two pH-measuring half-cells as a function of the pH value of a measuring medium in contact with the sensor comprises a second sensor zero-point that is different from the first sensor zero-point. In this way, during adjustment, not only the sensor zero-points, but also an average gradient of the two measuring chains consisting of the reference half-cell and the first measuring half-cell and of the reference half-cell and the second measuring half-cell can be determined.

BRIEF DESCRIPTION OF THE DRAWINGS

The present disclosure is explained in further detail below on the basis of the exemplary embodiments shown in the figures.

DETAILED DESCRIPTION

It is therefore an object of the present disclosure to specify a container with at least one sensor integrated into the container wall, said container allowing for a quick start of the process to be performed in the container and a sufficient measurement accuracy and quality of the measured values output by the sensor.

Figure 1:
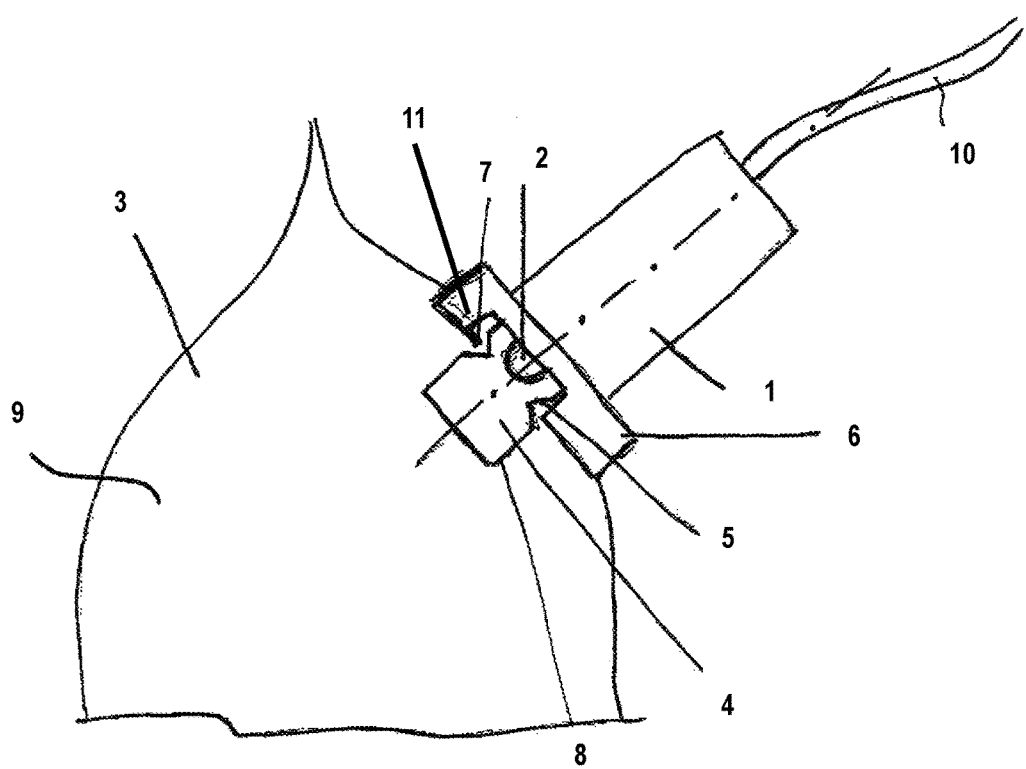
FIG. 1 shows a disposable process container, in the wall of which is integrated a sensor arrangement, according to a first exemplary embodiment.

FIG. 1 schematically depicts a first exemplary embodiment of a disposable container 3 with a sensor arrangement integrated into its wall. The disposable container 3 in the present exemplary embodiment is a pouch with a flexible wall, which can be used as, for example, a container for a fermentation process. The sensor arrangement comprises a sensor housing 1, into which a sensor 2 is integrated and on which said sensor is mounted. The sensor 2 may, for example, be an amperometric or potentiometric sensor, such as a potentiometric pH sensor, a potentiometric sensor comprising an ion-selective electrode, a glucose sensor, or a potentiometric or amperometric enzyme sensor or an amperometric oxygen sensor. The sensor 2 is designed to detect analog or digital measured values of one or more measured variables of a measuring medium in contact with the sensor 2 and to output them via the sensor cable 10.

The sensor housing 1 is attached to the flexible wall of the disposable container 3 via an adapter 6. The sensor housing 1 comprises a housing interior space 4 that surrounds the sensor 2 and is delimited by a housing wall 8. In the housing interior space 4, which is closed off (i.e., fluidly separated) from the container interior 9, a liquid may be contained for the damp storage of the sensor 2. This liquid may, for example, be a physiological buffer solution or another liquid. The housing wall 8 comprises a predetermined breaking point 5, which is designed in the present example as a notch extending around the cylindrical housing wall 8. The adapter 6 has a projection 7 oriented in the direction of the notch. The sensor housing 1 is mounted so as to be able to move in accommodating channel 11 axially and horizontally relative to the adapter 6. When commissioning the disposable container 3 and the sensor arrangement to perform a fermentation process, for example, the sensor housing 1 may be grasped from outside the process container 3 and moved with respect to the projection 7, such that said projection 7 abuts the housing wall 8 and opposes the movement of the housing with an opposing force, which acts on the housing wall 8 and causes the predetermined breaking point 5 to break, so that the portion of the sensor housing that protrudes into the process container 3 breaks along the predetermined breaking point 5. In the process, a fluid connection between the container interior space 9 and the housing interior space 4 is established, so that the sensor 2 may be brought into contact with a medium of the fermentation process, which is contained in the disposable container 3, in order to detect measured values. The liquid contained in the housing interior space 4 exits into the disposable container 3, which, as a rule, is the case with a physiological buffer solution. It is, moreover, advantageous if the housing 1 is designed such that the volume of liquid contained in the housing interior space 4 for damp storage is kept appropriately small.

The sensor arrangement of the exemplary embodiment illustrated in FIG. 1 also allows for the sensor 2 to be calibrated, verified, and/or adjusted prior to commissioning, i.e., prior, also, to opening the housing interior space 4 to the process container 3. In this case, the liquid contained in the housing interior space 4 is selected such that it comprises a defined and known value of the measured variable or of the several measured variables that may be measured by means of the sensor 2. For the calibration, verification, or adjustment, a measured value of the measured variable or of each measured variable is detected by means of the sensor 2 and appropriately analyzed for the calibration, verification, or adjustment of the sensor. Only afterwards is the housing wall 8 broken at the predetermined breaking point 5, and the connection of the sensor 2 with the container interior space 9 thus established.

The sensor arrangement described with reference to FIG. 1 may also be integrated into a process container with a stiff wall—for example, into a pipeline.

Figure 2:
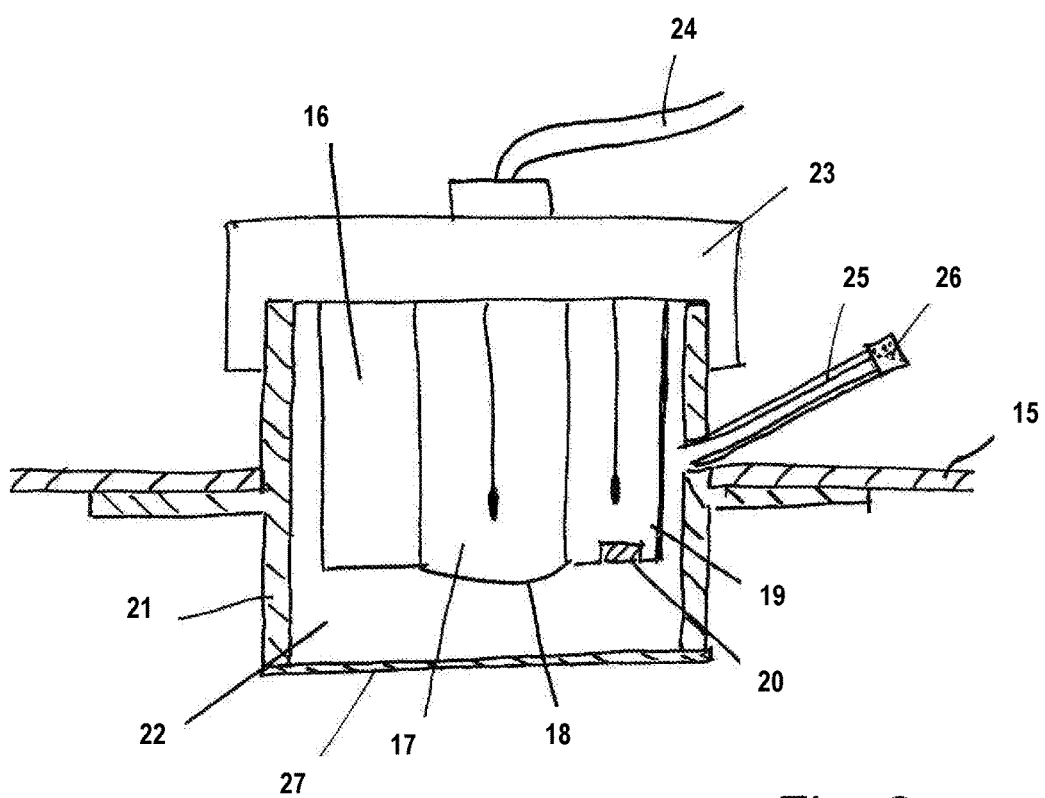
FIG. 2 shows a sensor arrangement according to a second exemplary embodiment.

FIG. 2 shows schematically another exemplary embodiment of a sensor arrangement integrated into a wall 15 of a disposable container. The sensor arrangement comprises a sensor 16, which in the present example is designed as a potentiometric pH sensor. Such a potentiometric pH sensor is known in single-use technology, e.g., from DE 10 2010 030 874 A1. The sensor 16 comprises a measuring half-cell 17 with a pH-sensitive diaphragm 18 and a reference half-cell 19 with a diaphragm 20. In order to ensure that the sensor 16 can be used immediately upon commissioning, it is advantageous to store the sensor 16 under damp conditions, i.e., in such a way that both the diaphragm 20 and the diaphragm 18 are wetted by a liquid. The sensor 16 is arranged in a housing comprising a housing wall 21 that surrounds a housing interior space 22 which is separated from the container interior space of the disposable container by the housing wall 21. The housing interior space 22 may be filled with a liquid for damp storage of the sensor 16. The housing is mounted on the wall 15 of the disposable container. On its rear side, i.e., on its side facing away from the container interior space, the housing is sealed in a liquid-tight manner by a housing cover 23. Through the housing cover 23 are guided the electrical connections of the sensor 16, which are connected to a sensor cable 24, via which the sensor 16 can output analog or digital measured pH values.

The housing also comprises a supply line 25, which ends in the housing interior space 22 and is closed off from the surroundings in a sterile manner by means of a sterile connector. Via the sterile connector, gases or liquids can be introduced into the housing interior space 22 or extracted from it in a sterile manner.

The wall region 27 of the housing wall 21, which faces the container interior of the disposable container, comprises a wall thickness that is reduced compared to the rest of the housing wall 21. This is dimensioned such that, in case of an over-pressure or an under-pressure that can be adjusted in the housing interior space 22, this wall region 27, as the predetermined breaking point, breaks, and, in this way, a connection is established between the housing interior space 22 and the container interior space of the disposable container, via which connection the sensor 16 can be brought into contact with the medium that is present in the container interior space. An over- or under-pressure may, for example, be produced by introducing a liquid or another pressurizing medium via the supply line 25 into the housing interior space 22 or by extracting medium from the housing interior space 22 via the supply line 25, and thereby a vacuum in the housing interior space 22 generated. In this last embodiment, liquid from the housing interior space 22 is prevented from getting into the disposable container.

The liquid contained in the housing interior space 22 may be used to calibrate, verify, or adjust the sensor 16 in the same manner as described with reference to the exemplary embodiment described in FIG. 1.

In another exemplary embodiment, the supply line 25 can be omitted in the sensor arrangement described in FIG. 2. In this embodiment, the sensor 16 may be mounted by means of a thread, for example, so as to be able to move axially relative to the housing wall 21 or 27. By moving the sensor 16 axially toward the wall region 27, the liquid contained in the housing interior space may be compressed, such that a breaking of the wall region 27 is effected.

While various embodiments of a disposable container and methods of constructing and using the same have been described in considerable detail herein, the embodiments are merely offered by way of non-limiting examples of the disclosure described herein. It will therefore be understood that various changes and modifications may be made, and equivalents may be substituted for elements and steps thereof, without departing from the scope of the disclosure. Indeed, this disclosure is not intended to be exhaustive or to limit the scope of the disclosure.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. Other sequences of steps may be possible. Such sequences may be varied and still remain within the scope of the present disclosure. Therefore, the particular order of the steps disclosed herein should not be construed as limitations of the present disclosure.

What is claimed is:

1. A container comprising:
    a container wall defining a container interior space;
    an adapter attached to the container wall and defining an accommodating channel from outside the container into the container interior space; and
    a sensor arrangement disposed in the container wall through the adapter, the sensor arrangement including:
        a housing having a housing wall defining a housing interior space and fluidly separating the housing interior space from the container interior space; and
        a sensor disposed in the housing interior space, the housing wall including a wall region structured as a predetermined breaking point;
    wherein the housing is axially movable along an axis of the accommodating channel or an axis of the housing;
    wherein the predetermined breaking point is embodied as a notch in the housing wall and is configured to deliberately rupture in the container interior space during movement of the housing relative to the adapter to fluidly connect the housing interior space with the container interior space.

2. The container according to claim 1, wherein the adapter includes an element that works together with the predetermined breaking point to open the housing toward the container interior space.

3. The container according to claim 1, wherein the adapter includes an element structured to oppose rotational movement or axial movement of the housing by means of a mechanical resistance.

4. The container according to claim 1, wherein the adapter includes an element structured to cut open the housing wall in the vicinity of the predetermined breaking point when the housing is moved axially or rotationally.

5. The container according to claim 1, wherein at least the section of the housing wall including the predetermined breaking point is a plastic.

6. The container according to claim 5, wherein the plastic is one of the group: PE, PP, PVDF, PFA, and a fluorine-containing plastic.

7. The container according to claim 1, wherein the sensor is structured to detect a value of at least one measured variable of a measuring medium.

8. The container according to claim 7, wherein the housing interior space is filled with a medium at least partially wetting the sensor, the medium having a predetermined value of the at least one measured variable.

9. The container of claim 8, wherein the medium is mixed with a liquid in the container interior space after the predetermined breaking point is deliberately ruptured.

10. The container according to claim 7, wherein the sensor is structured to detect values of several measured variables, and wherein the medium exhibits a respective predetermined value of each of the several measured variables.

11. The container according to claim 1, wherein the sensor includes several sensing elements of the same type.

12. The container according to claim 1, wherein the housing is guided in the accommodating channel so as to be able to rotate about an axis of the accommodating channel or an axis of the housing.

* * * * *